(12) United States Patent
Blackburn

(10) Patent No.: US 10,124,940 B2
(45) Date of Patent: Nov. 13, 2018

(54) SYSTEMS, METHODS, AND DEVICES FOR DISPENSING ONE OR MORE SUBSTANCES

(71) Applicant: Zolo Solutions, Inc., Las Vegas, NV (US)

(72) Inventor: Christopher Paul Blackburn, Las Vegas, NV (US)

(73) Assignee: Zolo Solutions, Inc., Las Vegas, NV (US)

( * ) Notice: Subject to any disclaimer, the term of this patent is extended or adjusted under 35 U.S.C. 154(b) by 0 days.

(21) Appl. No.: 14/725,969

(22) Filed: May 29, 2015

(65) Prior Publication Data

US 2015/0259110 A1    Sep. 17, 2015

Related U.S. Application Data

(63) Continuation-in-part of application No. 13/934,845, filed on Jul. 3, 2013, now Pat. No. 9,870,450.
(Continued)

(51) Int. Cl.
*G07F 9/02* (2006.01)
*G06F 19/00* (2018.01)
(Continued)

(52) U.S. Cl.
CPC .......... *B65D 50/00* (2013.01); *A61J 7/0076* (2013.01); *G06F 19/00* (2013.01);
(Continued)

(58) Field of Classification Search
CPC ..... B65D 50/00; G07F 17/0092; G07F 9/026; A61J 7/0076; A61J 1/03; A61J 2220/30; G06F 19/3462
See application file for complete search history.

(56) References Cited

U.S. PATENT DOCUMENTS 3,369,697 A   2/1968  Glucksman et al.
3,998,356 A  12/1976  Christensen
(Continued)

FOREIGN PATENT DOCUMENTS

JP    2001070405     3/2001
WO   WO2010/066456   6/2010

OTHER PUBLICATIONS

U.S. Appl. No. 13/934,845, Aug. 26, 2015, Office Action.
(Continued)

*Primary Examiner* — Patrick Cicchino
(74) *Attorney, Agent, or Firm* — Ray Quinney & Nebeker P.C.; Paul N. Taylor

(57) ABSTRACT

A secure dispensing device uses biofeedback to control release of a controlled substance. The secure dispensing device includes a housing with an access compartment that holds a controlled substance, the controlled substance including a first amount of the controlled substance to be dispensed according to one or more initial dispensation parameters; a controller that receives prescription bioinformation about a user and processes the prescription bioinformation to determine an adjusted dispensation parameter for the controlled substance to be dispensed, the initial dispensation parameter and the adjusted dispensation parameter of the controlled substance to be dispensed being different; a regulator that releases the controlled substance from within the housing; and an exit path with an opening that is sized for the controlled substance to be released outside of the access compartment.

20 Claims, 9 Drawing Sheets

Related U.S. Application Data

(60) Provisional application No. 61/699,516, filed on Sep. 11, 2012.

(51) Int. Cl.
- B65D 50/00 (2006.01)
- A61J 7/00 (2006.01)
- A61J 1/03 (2006.01)
- G07F 17/00 (2006.01)

(52) U.S. Cl.
CPC .......... *G06F 19/3462* (2013.01); *G07F 9/026* (2013.01); *G07F 17/0092* (2013.01); *A61J 1/03* (2013.01); *A61J 2200/30* (2013.01)

(56) References Cited

U.S. PATENT DOCUMENTS

| | | | |
|---|---|---|---|
| 4,292,115 A | 9/1981 | Jones et al. | |
| 4,293,845 A | 10/1981 | Villa-Real | |
| 4,361,408 A | 11/1982 | Wirtschafter | |
| 4,419,016 A | 12/1983 | Zoltan | |
| 4,483,626 A | 11/1984 | Noble | |
| 4,504,153 A | 3/1985 | Schollmeyer et al. | |
| 4,572,403 A | 2/1986 | Benaroya | |
| 4,573,606 A | 3/1986 | Lewis et al. | |
| 4,589,780 A | 5/1986 | Takebe | |
| 4,653,668 A | 3/1987 | Gibilisco | |
| 4,674,651 A | 6/1987 | Scidmore et al. | |
| 4,674,652 A | 6/1987 | Aten et al. | |
| 4,695,954 A | 9/1987 | Rose et al. | |
| 4,717,008 A | 1/1988 | Ellison et al. | |
| 4,725,997 A | 2/1988 | Urquhart et al. | |
| 4,872,591 A | 10/1989 | Konopka | |
| 4,971,221 A | 11/1990 | Urquhart et al. | |
| 5,036,462 A | 7/1991 | Kaufman et al. | |
| 5,084,828 A | 1/1992 | Kaufman et al. | |
| 5,102,008 A | 4/1992 | Kaufman et al. | |
| 5,110,008 A | 5/1992 | Moulding, Jr. | |
| 5,126,957 A | 6/1992 | Kaufman et al. | |
| 5,142,484 A | 8/1992 | Kaufman et al. | |
| 5,148,944 A | 9/1992 | Kaufman et al. | |
| 5,197,632 A | 3/1993 | Kaufman et al. | |
| 5,219,093 A | 6/1993 | Moulding, Jr. | |
| 5,221,024 A | 6/1993 | Campbell | |
| 5,230,441 A | 7/1993 | Kaufman et al. | |
| 5,335,816 A | 8/1994 | Kaufman et al. | |
| 5,392,952 A | 2/1995 | Bowden | |
| 5,543,063 A | 8/1996 | Walker et al. | |
| 5,611,456 A | 3/1997 | Kasper | |
| 5,647,507 A | 7/1997 | Kasper | |
| 5,710,551 A | 1/1998 | Ridgeway | |
| 6,018,289 A | 1/2000 | Sekura | |
| 6,108,588 A | 8/2000 | McGrady | |
| 6,163,737 A | 12/2000 | Fedor et al. | |
| 6,198,383 B1 | 3/2001 | Sekura | |
| 6,594,549 B2 | 7/2003 | Siegel | |
| 6,973,371 B1 | 12/2005 | Benouali | |
| 6,985,869 B1 | 1/2006 | Stoll et al. | |
| 7,002,476 B2* | 2/2006 | Rapchak | G06F 19/3462 340/309.16 |
| 7,048,141 B2 | 5/2006 | Abdulhay et al. | |
| 7,330,101 B2 | 2/2008 | Sekura | |
| 7,359,765 B2* | 4/2008 | Varvarelis | A61J 7/0481 221/265 |
| 7,454,267 B2 | 11/2008 | Bonney et al. | |
| 7,711,449 B2 | 5/2010 | Abdulhay et al. | |
| 7,715,277 B2 | 5/2010 | De La Huerga | |
| 7,720,569 B2* | 5/2010 | Forrester | G07F 11/00 700/231 |
| 7,743,923 B2 | 6/2010 | Conley | |
| 7,751,932 B1 | 7/2010 | Fedor | |
| 7,882,980 B1 | 2/2011 | Horn | |
| 7,885,725 B2 | 2/2011 | Dunn | |
| 7,896,192 B2 | 3/2011 | Conley et al. | |
| 7,944,342 B2 | 5/2011 | Sekura | |
| 7,978,564 B2 | 7/2011 | De La Huerga | |
| 7,996,106 B2 | 8/2011 | Ervin | |
| 8,068,934 B2 | 11/2011 | Saltsov | |
| 8,180,485 B2* | 5/2012 | Reckelhoff | A61G 12/001 700/237 |
| 8,666,539 B2 | 3/2014 | Ervin | |
| 8,752,728 B2 | 6/2014 | Tignanelli | |
| 8,818,820 B1 | 8/2014 | Mehdizadeh | |
| 9,014,427 B2* | 4/2015 | Bear | A61J 7/0076 348/135 |
| 9,014,847 B2 | 4/2015 | Dunn | |
| 9,542,534 B1* | 1/2017 | Ducatt | G06F 19/3462 |
| 9,572,748 B2* | 2/2017 | Lim | A61J 1/03 |
| 2003/0183642 A1 | 10/2003 | Kempker | |
| 2004/0019794 A1* | 1/2004 | Moradi | G06F 19/3462 713/185 |
| 2005/0096628 A1* | 5/2005 | Greeven | G06F 19/3406 604/504 |
| 2007/0012712 A1 | 1/2007 | Syiau | |
| 2008/0054007 A1 | 3/2008 | Mador | |
| 2009/0294521 A1 | 12/2009 | De La Huerga | |
| 2010/0004772 A1 | 1/2010 | Elfstrom et al. | |
| 2010/0030374 A1 | 2/2010 | Saltsov | |
| 2010/0258565 A1 | 10/2010 | Isaacson et al. | |
| 2011/0172812 A1 | 7/2011 | Joslyn | |
| 2012/0006700 A1 | 1/2012 | Geboers et al. | |
| 2012/0046970 A1 | 2/2012 | Potts | |
| 2013/0226339 A1 | 8/2013 | Ervin | |
| 2014/0074283 A1 | 3/2014 | Blackburn | |
| 2014/0074505 A1* | 3/2014 | Scanlon | G06Q 10/10 705/3 |
| 2014/0262918 A1 | 9/2014 | Chu | |
| 2014/0339248 A1 | 11/2014 | Reddy et al. | |
| 2014/0346184 A1* | 11/2014 | Bae | A61J 7/0076 221/1 |
| 2015/0081330 A1 | 3/2015 | Mann et al. | |
| 2015/0272825 A1* | 10/2015 | Lim | A61J 1/03 340/5.2 |
| 2015/0359711 A1* | 12/2015 | Ducatt | A61J 7/0076 221/13 |

OTHER PUBLICATIONS

Anonymous: "Ultimate tensile strength", Wikipedia, Jul. 11, 2013, XP055265025, Retrieved from: https://en.wikipedia.org/w/index.php?title=Ultimate_tensile_strength&oldid=501787147; Retrieved Apr. 13, 2016, 6 pages.

Anonymous: "Strength—Toughness", XP055265035, Cambridge, UK, Retrieved from: http://www.materials.eng.cam.ac.uk/mpsite/interactive_charts/strength-toughness/basic.html; Retrieved Apr. 13, 2016, 6 pages.

Anonymous: "Strength of materials", Wikipedia Sep. 7, 2012, XP055264821, Retrieved from: http://en.wikipedia.org/w/index.php?title=Strength_of_materials&oldid=511296893; Retrieved Apr. 12, 2016, 7 pages.

Anonymous: "Toughness", Wikipedia, Jul. 8, 2012, XP055264818, Retrieved from: http://en.wikipedia.org/w/index.php?title=Toughness&oldid=501306911; Retrieved Apr. 12, 2016, 2 pages.

U.S. Appl. No. 13/934845, Feb. 12, 2016, Office Action.
U.S. Appl. No. 13/934845, Jul. 8, 2016, Office Action.
U.S. Appl. No. 13/943,845, dated Apr. 20, 2017, Office Action.
U.S. Appl. No. 13/943,845, dated Jun. 15, 2017, Office Action.
U.S. Appl. No. 61/699,516, filed Sep. 11, 2012, Blackburn.
Application No. PCT/US2013/058861, International Search Report and Written Opinion, dated Feb. 19, 2014.

\* cited by examiner

SYSTEMS, METHODS, AND DEVICES FOR DISPENSING ONE OR MORE SUBSTANCES

CROSS-REFERENCE TO RELATED APPLICATIONS

This application is a Continuation-in-Part Application of U.S. patent application Ser. No. 13/934,845, entitled "DRUG DELIVERY REGULATOR" filed Jul. 3, 2013, which claims priority to U.S. Provisional Patent Application No. 61/699,516, entitled "DRUG DELIVERY REGULATOR" filed Sep. 11, 2012, the entire contents of which are incorporated herein by reference.

BACKGROUND

Medications are often taken for an intended purpose—as a remedy for a health problem. Unfortunately, this is not always the case. A serious issue exists with prescription drug misuse and abuse. Consequences include emergency room visits for accidental overdoses and admissions to drug treatment programs for drug addictions. Furthermore, the consequences may be lasting, with changes both to structure and function of the brain; a grim reality is that the consequences can be fatal.

Another problem with medications is that people may give their prescription drugs to friends or sell prescription drugs for money, thus supporting other people's self-medication, drug habits, and addictions. Exchange of pills is problematic because many pills look the same and one pill may easily be mistaken for another kind of pill. As a result, a person may suffer a serious reaction from unknowingly taking the wrong pill. Even if the person receives the intended pill, the dosage may be wrong because it lacks a doctor's proper care.

Sometimes the problem is not with taking pills; the problem is not remembering to take pills. A patient may forget the appropriate schedule for taking the medication. A patient may forget the proper dose or forget his or her individualized instructions. Thus, the patient may go without necessary medication and suffer as a result. Problems are not always isolated to adults either. Many children have unsupervised and unfettered access to their medications, leading to the same types of issues that challenge adults. Thus, for both young and old, drug use is a serious problem. With all of the problems, one may easily recognize that it is important to have the proper amount of medication, taken at the right time of day and with care by a proper authority, in order to have a healthy population.

BRIEF SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In an embodiment, a dispensing device with biofeedback includes a housing and an access compartment within the housing. The access compartment holds a controlled substance, including a first amount of the controlled substance. A controller included with the dispensing device receives prescription bioinformation about a user and processes the prescription bioinformation to determine a second amount of the controlled substance to be dispensed, the first amount and the second amount of the controlled substance to be dispensed being different. For releasing the controlled substance, including first and second amounts, an exit path and a regulator are provided with the dispensing device. The regulator releases the controlled substance from within the access compartment through the exit path, the exit path having an opening that is sized for the controlled substance to be released outside of the housing.

A method of dispensing one or more controlled substances housed within a dispensing device includes receiving prescription bioinformation about a user that relates to the controlled substance for the user; comparing the prescription bioinformation with stored prescription information; independently changing a first amount of the controlled substance to a second amount of the controlled substance based on the stored prescription and the prescription bioinformation, the first amount and second amount being different; and releasing the second amount of the controlled substance.

In another embodiment, a dispensing device with biofeedback includes a housing and an access compartment within the housing that holds a controlled substance. A controller included with the dispensing device receives a biometric identifier about a user and determines whether or not the biometric identifier is associated with the dispensing device. If the biometric identifier is authentic to the user, a regulator within the dispensing device releases a prescribed amount of the controlled substance from within the access compartment through the exit path, the exit path having an opening that is sized for the controlled substance to be released outside of the housing.

A method of authenticating a dispensing device may include receiving a biometric identifier about a user, and allowing further action associated with the dispensing device to be performed if the biometric identifier is associated with the dispensing device. Further action may include receiving an additional biometric identifier, receiving further prescription bioinformation about the user, releasing a first amount of a controlled substance, determining a second amount of the controlled substance, and releasing the second amount of the controlled substance, the first amount and second amount being different.

One or more acts, in whole or in part, may be performed automatically and without human intervention. For example, the biometric identifier may be automatically transmitted from a wearable sensor. Identifying information included in the biometric identifier may be passively obtained from a sensor that is worn, attached, or otherwise associated with the user and include one or more of heart information, blood information, and physiological trait information.

In yet another embodiment, a method of securing a secure dispensing device includes detecting a change of state of the secure dispensing device in real-time and sending state information regarding the state of the secure dispensing device to a microprocessor, and the processing the state information to determine if the state information exceeds a threshold value for the state information. If the state information exceeds a threshold value for the state information, the method further includes locking the secure dispensing device. The secure dispensing device may remain in a locked state until an unlock command is sent. In some embodiments, the unlock command may be sent after a lock interval has elapsed, after the state information returns to a value within the threshold value, upon instruction from a care provider, or combinations thereof.

Additional features and advantages of embodiments of the disclosure will be set forth in the description which follows, and in part will be obvious from the description, or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF DRAWINGS

In order to describe the manner in which the above-recited and other features of the disclosure can be obtained, a more particular description will be rendered by reference to specific embodiments thereof which are illustrated in the appended drawings. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

Figure 1:
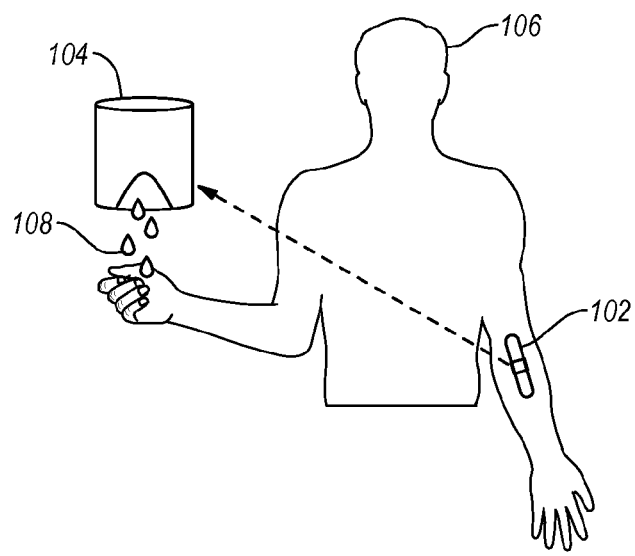
FIG. 1 illustrates a dispensing device releasing an amount of a controlled substance based on prescription bioinformation received from a bioinformation sensory device.

Medications are often taken for an intended purpose—as a remedy for a health problem. Unfortunately, this is not always the case. A serious issue exists with prescription drug misuse and abuse. Consequences include emergency room visits for accidental overdoses and admissions to drug treatment programs for drug addictions. Furthermore, the consequences may be lasting, with changes both to structure and function of the brain; a grim reality is that the consequences can be fatal.

Another problem with medications is that people may give their prescription drugs to friends or sell prescription drugs for money, thus supporting other people's self-medication, drug habits, and addictions. Generally speaking, exchange of pills is problematic because many pills look the same and one pill may easily be mistaken for another kind of pill. As a result, a person may suffer a serious reaction from unknowingly taking the wrong pill. Even if the person receives the intended pill, the dosage may be wrong because it lacks a doctor's proper care.

Sometimes the problem is not with taking pills; the problem is not remembering to take pills. A patient may forget the appropriate schedule for taking the medication. A patient may forget the proper dose or forget his or her individualized instructions. Thus, the patient may go without necessary medication and suffer as a result. Problems are not always isolated to adults either. Many children have unsupervised and unfettered access to their medications, leading to the same types of issues that challenge adults. Thus, for both young and old, drug use is a serious problem. With all of the problems, one may easily recognize that it is important to have the proper amount of medication, taken at the right time of day and with care by a proper authority, in order to have a healthy population.

A secure dispensing device and associated methods of use are discussed herein that enable proper care and administration of prescription medications through principles of biofeedback and compliance notifications. Biofeedback uses electronic sensory feedback and monitoring to allow enhanced control over autonomic nervous system function as measured by sensory information, for example, by skin conductance (sweating), muscle tension, skin temperature, heartrate, or combinations thereof. Conventional biofeedback devices receive the sensory information about the user and may present the information to the user graphically andor textually to help the user gain control of body and health. For example, a user andor care provider may be made aware of conditions otherwise unknown, such as abnormal heart rate andor abnormal nervous system activity based on the sensory information received by the device andor presented to the user. Thus, the user can cognitively make changes based on the sensory information. As used herein, while the term "user" may refer primarily to a patient it may also refer to an intended recipient of the controlled substance, and the term "care provider" may be any person authorized to provide care to the user. In some embodiments, a user and a care provider may be the same person, such as a nurse in hospice care. The nurse may be authorized to receive the controlled substance to provide to the patient, while also receiving notifications if the patient attempts to access the controlled substance outside the parameters of their prescription.

By incorporating principles of biofeedback, namely, by receiving sensory information and processing the sensory information, a secure dispensing device according to the present disclosure may change the dispensation (e.g., quantity, frequency, or both) of one or more controlled substances intended for the patient. As used herein, the term "controlled substance" should be understood to encompass any prescription medication prescribed by a doctor andor provided by a pharmacist, as well as any other substance that may be hazardous to an individual in improper dosages. In some embodiments, a controlled substance may be any substance dispensed by a secure dispensing device according to the present disclosure. The user need not cognitively recognize the sensory information presented.

In some embodiments, the dispensing device acts in place of the user andor care provider and makes alterations to the dispensation of the controlled substance that affect body and health. For example, blood levels of a particular substance in the user's blood may be monitored to assist in dynamically determining appropriate dosage quantities of a controlled substance. As used herein, the term "user" may refer to the patient andor intended recipient of the controlled substance, and the term "care provider" may be any person authorized to provide care to the user. In some embodiments, a user and a care provider may be the same person, such as a nurse in hospice care. The nurse may be authorized to receive the controlled substance to provide to the patient, while also receiving notifications if the patient attempts to access the controlled substance outside the parameters of their prescription.

In other embodiments, the dispensing device may communication one or more notifications to a user andor care provider that an alteration to the dispensation of the controlled substance may be appropriate. For example, consistent failure of compliance with the prescribed medication schedule may prompt a notification to a doctor to alter the medication schedule to better facilitate compliance. In yet other embodiments, the dispensing device may communication one or more notifications to a care provider that the dispensing device or user may require attention. For example, repeated andor unsuccessful attempts to access the controlled substance within the secure dispensing device may prompt the secure dispensing device to deliver a notification or other alert to a care provider to confirm the status of the secure dispensing device (e.g., a warning that the secure dispensing device may be stolen or damaged) or the user (e.g., a warning that the user may be attempting to access the controlled substances outside the parameters of their prescription).

Similar principles of biofeedback may also be used to authenticate a user to one or more secure dispensing devices. To take actions based on biofeedback, a secure dispensing device may receive prescription bioinformation andor a biometric identifier from an external source. Prescription bioinformation is any kind of measurable information about a user that pertains to health of the user. A biometric identifier includes unique measurable information associated with a user and that may be used to authenticate the user to the dispensing device. There may be an overlap between certain biometric identifiers and certain types of prescription bioinformation such that the two types of information are the same.

In some embodiments, a secure dispensing device that uses biofeedback includes a housing and an access compartment within the housing. The access compartment holds a controlled substance, including at least a first amount of the controlled substance. A controller included with the secure dispensing device receives prescription bioinformation about a patient from an external source and processes the prescription bioinformation to determine a second amount of the controlled substance to be dispensed, the first amount and the second amount of the controlled substance to be dispensed may be different. For releasing the controlled substance, including first andor second amounts, an exit path and a regulator are provided with the secure dispensing device. The regulator releases the controlled substance from within the access compartment through the exit path, the exit path having an opening that is sized for the controlled substance to be released outside of the housing to a user.

In some embodiments, the controller receives the prescription bioinformation in a continual manner or in a real-time manner. Also, the prescription bioinformation may be transmitted to and stored in a computer network for third parties to access. To enable the user to have access rights to the controlled substance, an authentication receiver may receive authentication input from the user. The authentication input may be received, for example, from a passive biometric sensor.

A method of dispensing one or more controlled substances housed within a dispensing device includes receiving prescription bioinformation about a user that relates to the controlled substance for the user; comparing the prescription bioinformation with stored prescription information; independently changing a first amount of the controlled substance to a second amount of the controlled substance based on the stored prescription and the prescription bioinformation, where the first amount and second amount may be different; and releasing the second amount of the controlled substance.

In some embodiments, the method may include further steps, such as changing a time for dispensing, changing to a different controlled substance to be dispensed, locking the secure dispensing device, alerting the user andor care provider, authenticating the user using a biometric identifier, removing access rights from the user, and granting access rights to a third party, such as a care provider. In some embodiments, the user andor third party with access rights may override the determination of the second amount of the controlled substance.

In another embodiment, a secure dispensing device with biofeedback includes a housing and an access compartment within the housing that holds a controlled substance. A controller included with the secure dispensing device receives a biometric identifier about a user and determines whether or not the biometric identifier is associated with the secure dispensing device. Based on the biometric identifier, a regulator within the dispensing device releases a prescribed amount of the controlled substance from within the access compartment through the exit path, the exit path having an opening that is sized for the controlled substance to be released outside of the housing.

A method of authenticating a dispensing device may include receiving a biometric identifier about a user, and allowing further action associated with the dispensing device to be performed if the biometric identifier is associated with the dispensing device. Further action may include receiving an additional biometric identifier, receiving further prescription bioinformation about the user, releasing a first amount of a controlled substance, determining a second amount of the controlled substance, and releasing the second amount of the controlled substance, the first amount and second amount being different.

One or more acts, in whole or in part, may be performed automatically and without human intervention. The biometric identifier may be automated by being automatically transmitted from a wearable sensor. The identifying information included in the biometric identifier may be passively obtained from a biometric sensory device that is worn, attached, or otherwise associated with the user. The identifying information may include one or more of heart information, blood information, and physiological trait information.

FIG. 1 illustrates a sensor 102 configured to communicate with a secure dispensing device 104. The sensor 102 may be worn, carried, or affixed to a user 106 who is authorized to receive a controlled substance 108 dispensed by the secure dispensing device 104. The user 106 may receive an amount of the controlled substance 108 at predetermined intervals from the secure dispensing device 104 based on prescription bioinformation received andor stored in the secure dispensing device 104 about the user 106. The amount of the controlled substance 108 dispensed by the secure dispensing device 104 may be changed from a previously prescribed amount because of the prescription bioinformation received. Alternatively, or in addition, the user 106 may receive the amount of controlled substance 108 from the secure dispensing device 104 based on a successful authentication through a biometric identifier. The prescription bioinformation andor a biometric identifier may be received from a sensor 102 that is worn, attached, or otherwise associated with the user 106. As shown, the sensor 102 may be in the form of, or included as part of, an adhesive bandage that adheres to skin of the user 106. Other types of devices besides sensors and other forms of attachmentsassociations besides patch adherence to the user are anticipated.

Figure 2:
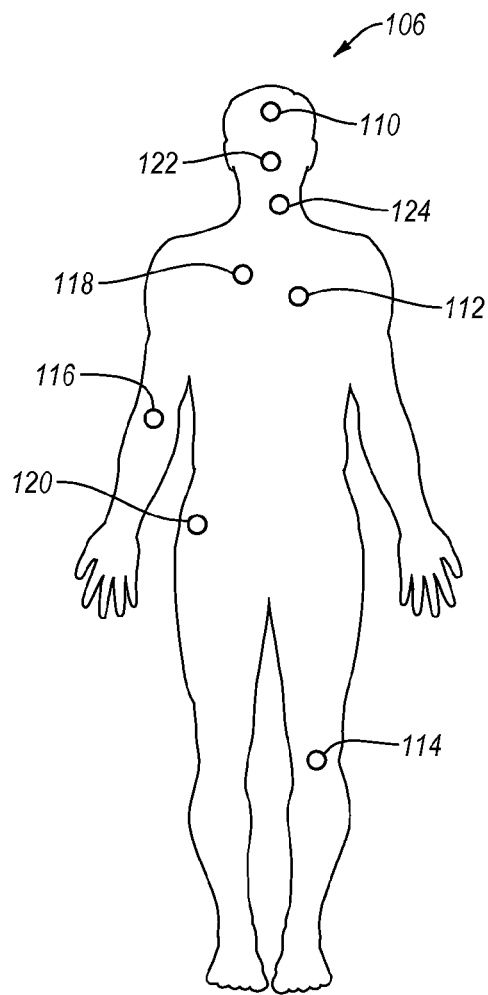
FIG. 2 illustrates various types of prescription bioinformation.

A host of information from the body is available for use as prescription bioinformation. This includes, as illustrated in FIG. 2, information from a nervous system 110, cardiovascular system 112, skeletalmuscular system 114, integumentary (i.e., hair, skin, and nails) system 116, digestive system 118, immunelymphatic system 120, respiratory system 122, endocrine system 124, or combinations thereof. Nervous system 110 information may include electrical information from the brain, spinal cord, and peripheral nerves regarding the detection and processing of sensory information and the activation of bodily responses. Cardiovascular system 112 information may include heart rate; blood pressure; volume; core body temperature; hydration levels; levels of glucose, glutamate, oxygen, triglycerides, other nutrients, other foreign elements including other medications andor drugs in the blood; and combinations thereof. Skeletalmuscular system 114 information may include facial features that indicate emotions and expressions, postures such as standing and sitting and other movements of the body, differential body temperatures, and other information regarding muscular response andor functioning. Integumentary system 116 information may include skin temperature, electrical changes (e.g., capacitance) in skin, other information regarding changes in the dermis, and combinations thereof. Digestive system 118 information may include the presence andor concentrations of particular enzymes, proteins, or other components of urine content, stool content, bile content, saliva content, or combinations thereof. As used herein, the digestive system 118 should be understood to include the urinary system. Immunelymphatic system 120 information may include measuring pathogen presence andor concentration, inflammation, white blood cell count, other immune response indicators, or combinations thereof. Respiratory system 122 information may include breathing rate, peak flow measurements, exhalation contents (e.g., oxygen and carbon dioxide ratios), voice information such as resonance and patterns, breath volume, other information nasal and lung functioning, or combinations thereof. Endocrine system 124 information may include hormone levels in the body.

Bioinformation that is unique about the user may be used as a biometric identifier to authenticate the user to the dispensing device. A biometric identifier may be passive or active. A passive biometric identifier is a characteristic or feature that is uncontrolled, unobtrusively measurable, and able to be independently obtained or measured so as to require no interaction by the user. The user may not even know that the process of identification or verification takes place. An active biometric identifier, on the other hand, is based on required actions of the user and therefore requires cognitive participation or cooperation. Whether active or passive, a biometric identifier is obtainable identifying information about the user's body and difficult to circumvent since imposters are a concern.

Passive biometric identifiers include, for example, reading a unique heart wave or electrical field of a portion of an individual (e.g., NYMI BAND HEARTID), DNA, andor using some forms of facial recognition technology that do not require participation of the user (cameras associated with user). Active biometric identifiers include, for example, retinal scans, voice and vocal resonance recognition, hand gestures, and facial recognition technology that may include participation of the user.

Sensory devices that collect or find information of the body may incorporate technology involving electrocardiography (EEC), electroencephalography (EEG), electromyography (EMG), photoplethysmography (PPG), graphene-based sensors, microelectromechanical sensors (MEMs), temperature sensors, vibration sensors, liquid sensors, volumetric sensors, other types of sensors, pulse oximetry, microfluidics, nanofluidics, accelerometers, gyroscopes, blood-based microliter labs, sweat test channels, contact microphones that capture sound patterns (e.g., from internal organs), and breathalyzers. Each technology may be used independently or in combination with other types of technology. Also, each technology may be used multiple times for one aspect of the body or for multiple aspects of the body. Moreover, more than one type of technology may be used to collect prescription bioinformation and make a prescription assessment.

Sensory devices that collect information of the body may include all sorts of devices, including invasive, non-invasive, skin-permeable, non-permeable in skin, and skin embedded types. Sensory devices may be worn, attached, or otherwise associated with the user. Sensory devices include, for example, patches, adhesive bandages (i.e., BANDAIDs), sensors that snap to clothing, custom clothing, thermal underwear, underclothing, smart fabric sensors in strap or clothing form, belts, waist bands, chest bands, wrist bands, watches (e.g., smartwatches including APPLE WATCH), headsets, headgear, headphones, glasses, earbuds, asthma inhalers, ingestible sensors, gel insoles for footwear, and cameras (e.g., cameras attached to the user's watch).

With information readily obtainable, any number of health problems and their associated prescriptions may be addressed. For example, one or more of brain seizure medication, panicanxiety medication, heart medication, pain medication, sleep medication, stress/psychological medication, cancer medication, and diet aids may be controlled. In some embodiments, a prescription may be switched to an entirely different prescription, thus allowing more than one type of health condition to be targeted as needed.

Figure 6:
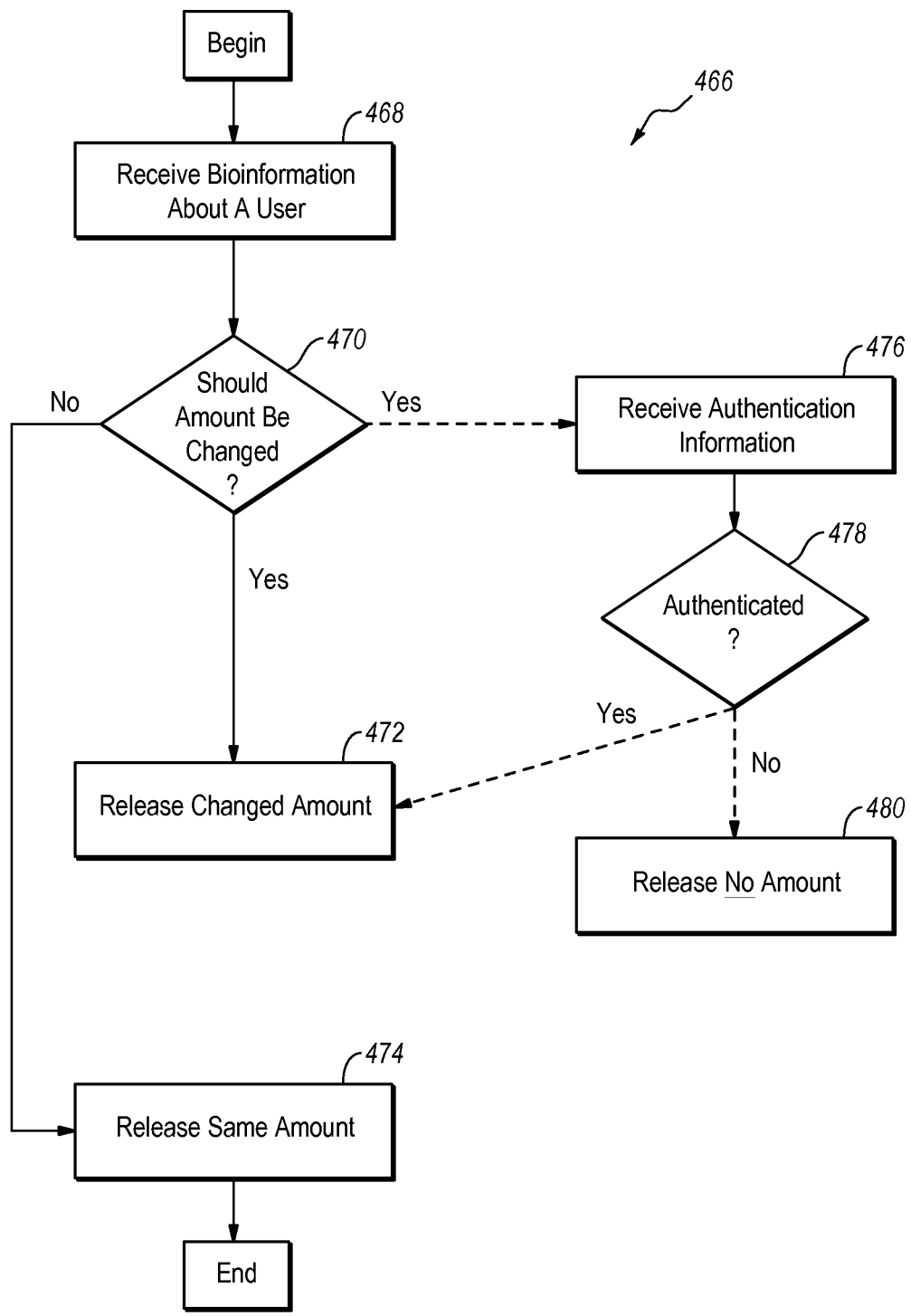
FIG. 6 is a flowchart illustrating a method for releasing a different amount of a controlled substance.

A secure dispensing device may be associated with a network, such as a computing cloud, to store up-to-date information on prescription related information and thereby facilitate remote access by third parties. Information, including prescription bioinformation, biometric identifiers, and directives regarding changes to a controlled substance, may be transmitted in encrypted form or other secure forms. FIG. 2 illustrates an example flow diagram of a system 100 that includes prescription bioinformation 126 provided by the sensor 102 or similar sensor of FIG. 1 to the secure dispensing device 104, and a network 128 that provides data communication between a plurality of devices such as a server 130 and computing device 132. The sensor 102 may be or include one or more bioinformation sensory devices. A bioinformation sensory device may take a form of, for example, a wristband 134, an adhesive bandage 136, head gear 138, and clothing 140, and other forms presented herein. The system 100 includes data flows that may occur when performing a method for making changes to an amount of a controlled substance and releasing the changed amount, a method for securing a secure dispensing device, or other methods including communication between the device and one or more remote computing devices. FIG. 6 is a flowchart for a method 466 of changing an amount of a controlled substance and releasing the changed amount using the system 100 depicted in FIG. 3 or a similar system. The method 466 will be described in relation to FIG. 6.

Figure 3:
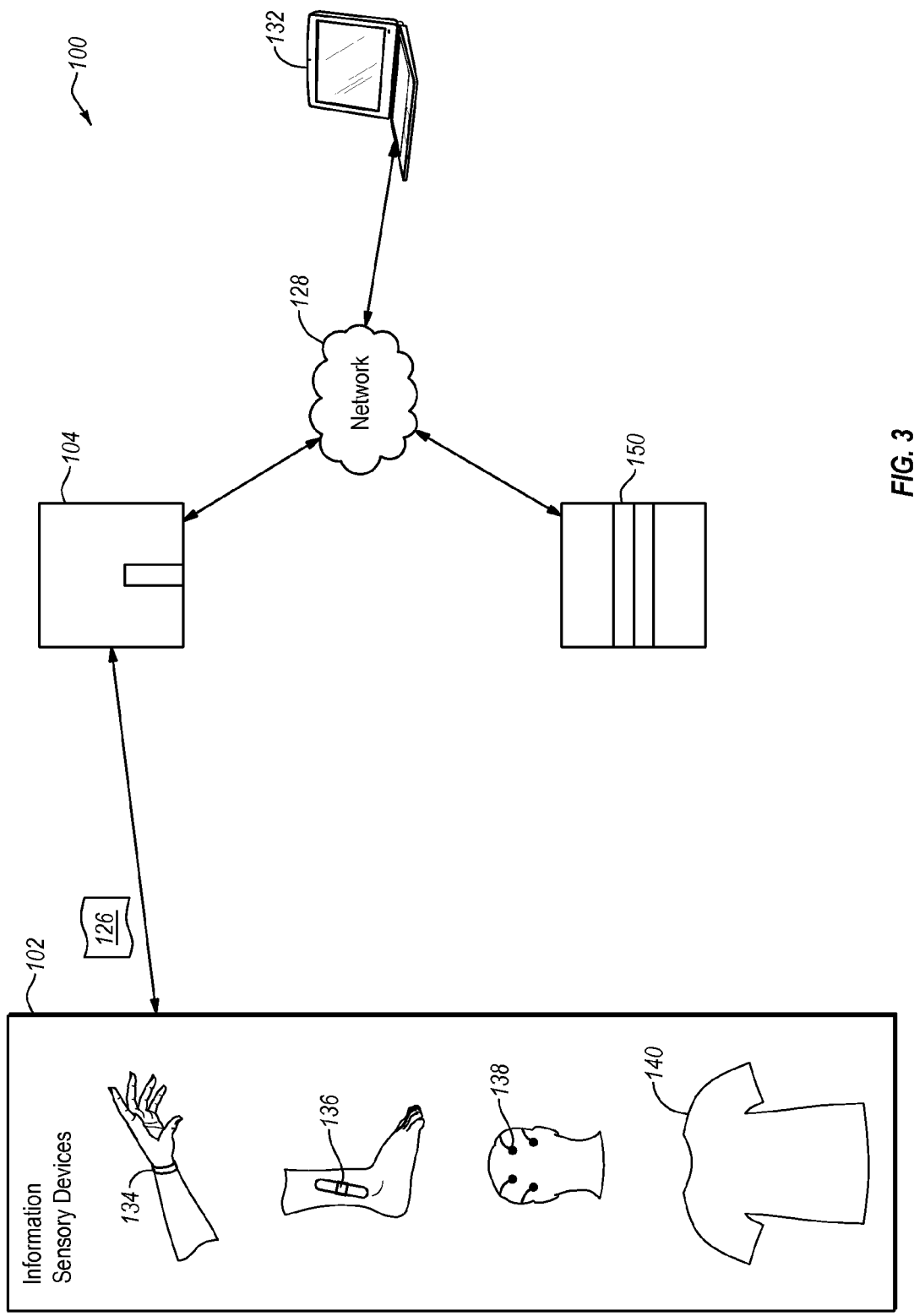
FIG. 3 illustrates a system wherein prescription bioinformation is received by a dispensing device.

Referring to FIG. 3, a sensor 102 having an information sensory device receives or senses prescription bioinformation 126 from one or more systems of the user's body 106 (such as described in relation to FIG. 2). The prescription bioinformation 126 is sent to the secure dispensing device 104. The prescription bioinformation 126 may be processed by the secure dispensing device 104 andor the server 130 to determine an amount of prescription substance to be released. If the server 130 performs the processing, the prescription bioinformation 126 may be sent to the server 130 from the secure dispensing device 104 via the network 128. Prescription bioinformation 126 may flow in the opposite direction as well, from server 130 to the sensor 102 or bioinformation sensory devices, for example, for real-time comparison against previously collected prescription bioinformation, storage in a data storage device, authentication purposes, or for other purposes. In an embodiment, processing the prescription bioinformation 126 may include a doctor or other care provider using computing device 132 to send information and directives over the network 128 to either the secure dispensing device 104 andor the server 130. Data flow that involves the doctor's computing device 132 is represented by dotted lines.

Figure 4:
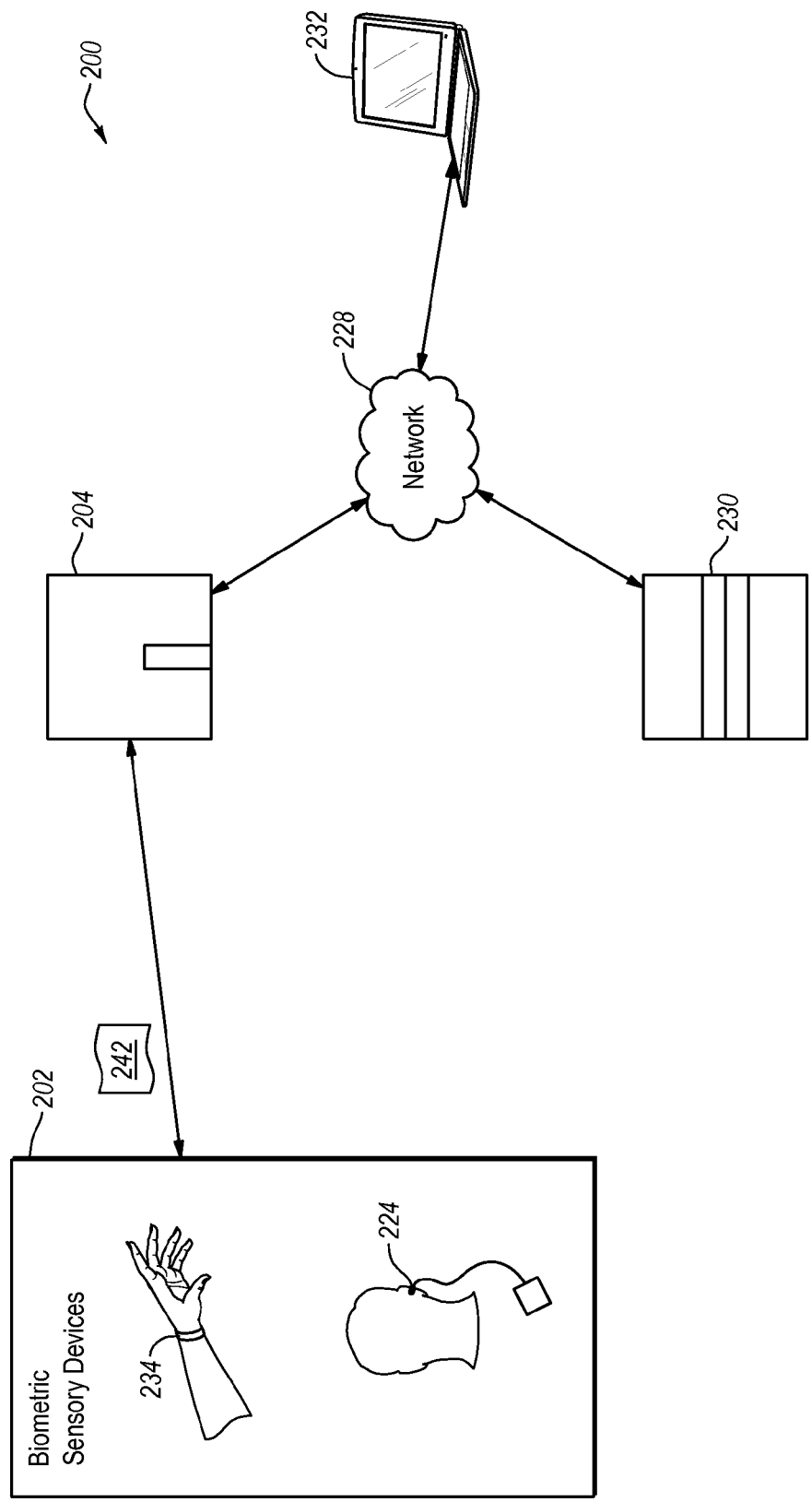
FIG. 4 illustrates a system wherein a biometric identifier is received by a dispensing device.

In some embodiments, a biometric identifier is required for purposes of releasing the controlled substance, but not for making changes to the dispensation of the controlled substance from the secure dispensing device. Processing may be isolated to authentication of the user for releasing a prescribed amount of the controlled substance. Turning to FIG. 4, a system 200 is shown including a biometric identifier 242 sent by a sensor 202 having one or more or biometric sensory devices to a secure dispensing device 204; and a network 228, server 230, and computing device 232, which may be similar to that described in relation to FIG. 3. Biometric sensory devices may include, for example, a sensory wristband 234, earbuds 244, and other sensory devices presented herein. The system 200 represents data flows that may occur when performing a method for authenticating a biometric identifier and releasing the prescribed amount.

A sensor 202 receives or senses a biometric identifier 242 from the user's body. The biometric identifier 242 is sent to the dispensing device 204. The biometric identifier 242 may be compared to stored information by the dispensing device 204 andor the server 230 to determine whether the biometric identifier 242 is authentic to the user. If the server 230 performs the processing, the biometric identifier 242 may be sent to the network 228, and from the network 228, sent to the server 230. The biometric identifier 242 may flow in the opposite direction as well, from server 230 to the sensor 202. In some embodiments, processing may involve a doctor using computing device 232 to send information and directives over the network 228 to either the secure dispensing device 204 andor the server 230.

Receiving bioinformation may occur in a continual manner while a sensor 102, 202 is in data communication (either via a network, a direct wired connection, or a direct wireless connection) with the secure dispensing device 104, 204, such that bioinformation is received on an on-going basis. However, the data communication may experiences interruptions. For example, interruptions may come in the form of human interventions, such as a human pressing a button used to start and stop communications. An interruption could also come in the form of external forces, such as requiring solar energy to power the secure dispensing device and losing power when solar energy is lost. Processes may have interruptions at any time the secure dispensing device is working or functioning. For example, the process of changing a prescription may be interrupted such that the process stops and a second interruption is required to continue the process.

In addition to operating in a continual manner, processing andor communication may occur in real-time. As used herein, "real-time" should be understood to mean processing andor communication that occurs on demand in response to a user interaction. The secure dispensing device may be in communication with a network andor an external computing device, such as a server andor the doctor's computer, substantially continuously or may connect to a network or external computing device upon receiving a user interaction. In another example, the secure dispensing device may remain activated, receiving prescription bioinformation in a continuous manner, but only communicate with the network andor external computing device when a user interacts with the secure dispensing device. A user interaction may include attempting to dispense the controlled substance, attempting to open the secure dispensing device, moving the secure dispensing device, or otherwise altering a state of the secure dispensing device. For either a continual manner or real-time manner, the processing of information may occur in the secure dispensing device, in the server, in the doctor's computing device, or a combination thereof.

As the sensor 202 receives andor collects the biometric identifier 242 from the user's body, the biometric identifier 242 is sent, to the secure dispensing device 204. The biometric identifier 242 may be processed by the secure dispensing device 204 to authenticate the sensor 202 andor user, thereby determining whether or not the biometric identifier 242 is associated with the dispensing device 204 and allowing further action associated with the secure dispensing device 204 to be performed based on the biometric identifier 242 received being correct. In some embodiments, the correct biometric identifier 242 is required before any amount of prescription substance is to be released.

In some embodiments, the sensor 202 may be activated at certain times, such as at a time prior to when the prescribed amount of the prescription substance is to be released. In other embodiments, biometric identifiers 242 are substantially continuously transmitted by the sensor 202. However, an embodiment accounts for interruptions similarly to the system for bioinformation sensory devices (such as in FIG. 3), such as human intervention and external forces, may be used to start and stop communications from biometric sensory devices in the sensor 202 or cause cessation during processing.

The biometric identifier 242 may be sent locally to the secure dispensing device 204. The biometric identifier 242 may be sent via a network 228 to a server 230 andor computing device 232, as shown in FIG. 4. The biometric identifier 242 and related information may, therefore, be stored andor processed in the server 230 andor computing device 232 in part or in whole via the network 228. Information related to the biometric identifier 242 may flow in the opposite direction as well, from server 230 andor computing device 232 to the secure dispensing device 204 andor sensor 202.

Figure 5:
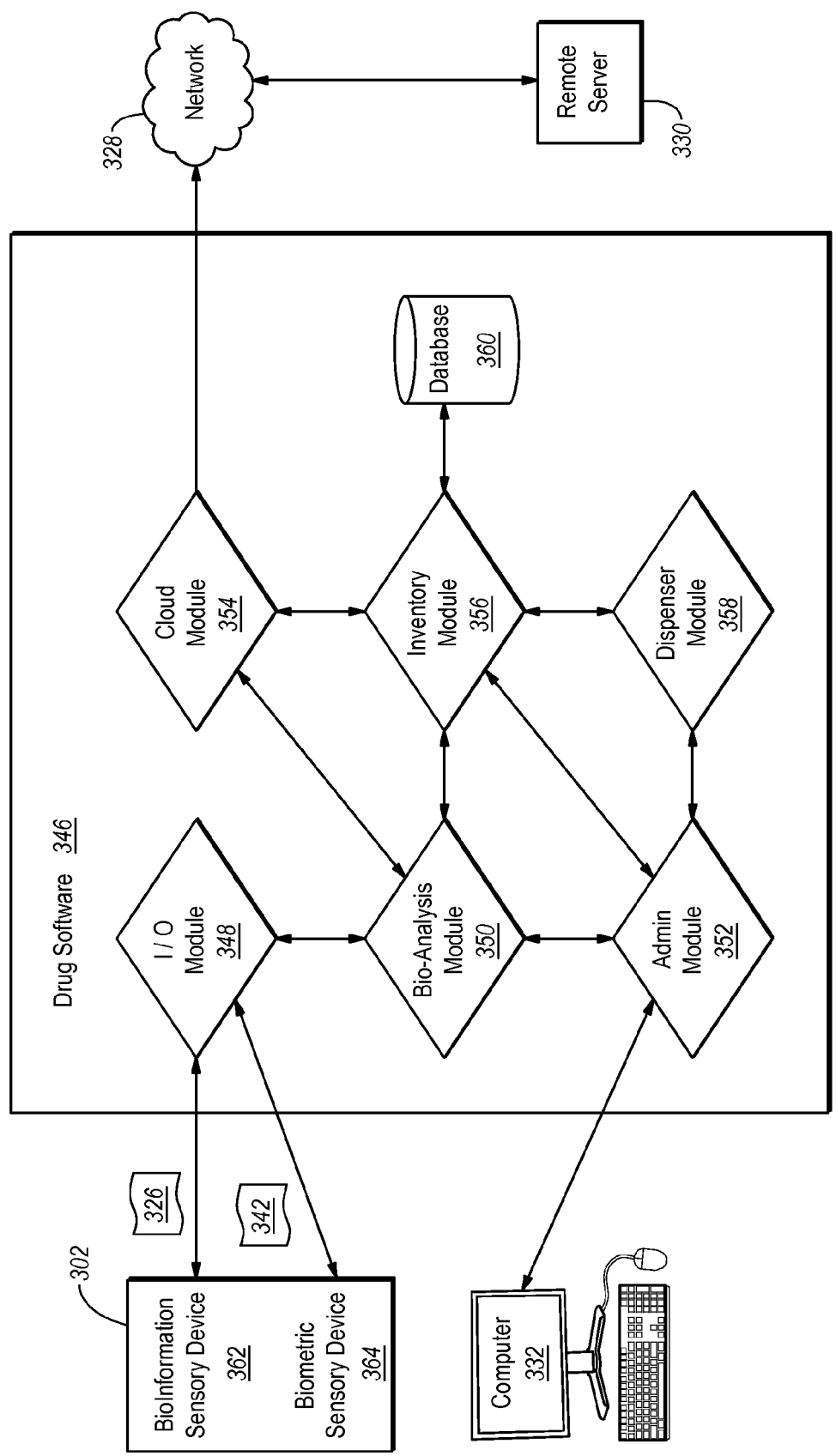
FIG. 5 illustrates drug software that may be implemented with a dispensing device.

In processing the prescription bioinformation 126, the secure dispensing device 104 may perform a variety of actions through the network by cellular access, by Bluetooth technology, direct connectivity, or other known ways of modern communication. Processing of the prescription bioinformation 126 may be performed with the implementation of drug software 346 schematically depicted in FIG. 5. In some embodiments, the software 346 may be in communication with a sensor 302 including a bioinformation sensory device 362, biometric sensory device 364. In other embodiments, the software 346 may also be in communication with a computer 332, network 328, and remote server 330. Modules of the software 346 include an I/O module 348, bio-analysis module 350, admin module 352, cloud module 354, inventory module 356, dispenser module 358, and database 360.

As used herein, the term "module" can refer to software objects or routines that execute on a computing system. The different modules, engines, and services described herein may be implemented as objects or processes that execute on the computing system (e.g., as separate threads). For changing a dispensation of the controlled substance from a first amount to a second amount, I/O module 348 may first receive prescription bioinformation from bioinformation sensory device 362. In bio-analysis module 350, the prescription bioinformation 326 may be compared with information stored in a database 360. The information may also be stored at the remote server 330 that is accessed by the cloud module 354 over a network 328.

Information stored may regard a current prescription and information about the prescription, including health factors about the user and information about the controlled substance. The prescription bioinformation may be compared with stored information to make a determination about whether or not the first amount should be changed to a second amount, and if so, what the second amount should be. The prescription bioinformation may further be compared with other information, such as information that relates to the dispensing device itself, such as its location, and whether it shows signs of tampering. In an example, a stored heart rate of the user may be compared with prescription bioinformation that includes heart rate of the user to determine whether or not the first amount of heart medication should be increased or decreased. In another example, the stored heart rate of the user, stored electrical activity of the user's skin, and stored facial recognition features are compared with corresponding heart rate, electrical activity of skin, and facial recognition features included in the prescription bioinformation. Based on this comparison, it can be determined whether or not to increase or decrease anti-anxiety medication.

A variety of other information may be stored. Information about the controlled substance may include, for example, name of contents, dosage, display information, number of pillssubstancecontents provided, amount of pillssubstancecontents remaining, expiration date, side effects, drug interactions, dosing instructions, dosing concentration, dosing schedule, time of delivery, countdown timer until the next dose, contraindications, sorting instructions for displayed information, refill information, and time the pillssubstancecontents were dispensed.

Information stored may further relate items of interest, such as the secure dispensing device's identification number, a user ID number, prescribing health care professional information, administrative user contact information, security codes, locking mechanism information, locking and unlocking secure dispensing device information, information on receiving, information on dispensing, information on regulating, patient information, multiple sets of patient information, password, passcode, validation user input, identifiable user input, biometric identifier, audio output, reminder alarm, separate key, RFID tag, attempts at unauthorized access to the secure dispensing device, indicator of damage to the secure dispensing device, location of the secure dispensing device, programming user information, time to activate the secure dispensing device, information on activating parts of the secure dispensing device, information of various sensors inside the secure dispensing device, sterilization information, encryption information and other security features, inputs for circumventing security features, any information that can facilitate legal and proper patient medication in accordance with prescriptions by authorized medical personnel. Specific information on the user may include age, sex, height, weight, medical history, diet, sleep patterns, exerciseactivity, as well as other information. The information list provided is in no way meant to be limiting.

Along with changing from a first amount of the controlled substance to a second amount of the controlled substance, bio-analysis module 350 may determine a variety of other changes or outcomes. For example, the first controlled substance may be changed to an entirely different, second controlled substance. If the secure dispensing device contains only the first controlled substance, the dispensing device may be locked and a notification displayed to the user andor care provider informing him or her that a new controlled substance must be taken. The secure dispensing device may be locked if a prescribed dose should not be taken at a certain prescribed time, or in other words, that the prescribed dose at a particular time should be skipped.

Another change may include changing the time of day or frequency by which the controlled substance must be taken. Further change may include changing the access rights to a third party, for example, if the received prescription bioinformation indicates levels that are extremely disparate with the stored information such that the user should have access rights removed.

As part of making changes, the bio-analysis module 350 may perform searches using online search tools including visiting sites that offer virtual medical related services. Information from virtual medical related services may be downloaded and stored on the server 330 or in the database 360. Such acts may be performed by the cloud module 354.

After a change has been made, an alert may be communicated to the user andor care provider through the I/O module 348. For example, a display on the secure dispensing device may convey the change. Alerts may include, for example, sounds, lights, and notifications sent to electronic devices. Other types of alerts are anticipated, such as communications remote from the secure dispensing device, such as SMS text messages to a user andor care provider's cellular phone, emails, updates pushed to an application on a computing device, or other communications not displayed on the secure dispensing device.

Instead of changing the controlled substance, a change may occur to third party privileges over the controlled substance, such as third party privileges represented by computer 332 having access to admin module 352. Third party privileges are typically designated for a doctor to communicate directives from the admin module 352 which are then processed in the bio-analysis module 350. For example, a doctor may send updates, directives, and information to be processed. The doctor may request that a change in prescription be processed immediately, rather than waiting for a set time for sensing prescription bioinformation. The doctor may request further information from the dispensing device, override decisions that are made by the dispensing device, and modify prescription information at any given time or circumstance. Third party privileges typically granted to the doctor may further include supplying information to the inventory module 356 where they may be stored in the database 360. Such information may include, for example, updated prescription information, update comparison data, and newly acquired patient data. In processing changes, the bio-analysis module 350 may request input from a doctor, request further information from a doctor, and send notifications to a doctor.

As described herein, the correct biometric identifier may be required for dispensing the controlled substance and/or receiving prescription bioinformation and then dispensing the controlled substance. For authenticating the user, I/O module 348 receives a biometric identifier 342 from biometric sensory device 364. In the bio-analysis module 350, the biometric identifier 342 is compared to user information that is stored in the database 360 and accessed through the inventory module 356. Alternatively, user information may be stored in the remote server 330 and accessed by the cloud module 354 through the network 328. Proper authentication requires that the biometric identifier match corresponding information stored on the remote server 330 or database 360. Authentication may be performed only once, before each preset time of release, at predefined intervals of time, at random times, upon triggered events, upon a user interaction, or combinations thereof. A triggered event may be, for example, when a first amount of the controlled substance is to be changed to a second amount. A doctor, or other third party with authority, may use computer 332 to access the admin module 352 and set times required for authentication.

For dispensing the controlled substance, secure dispenser module 304 is provided and may be controlled either by a party with privileges to the admin module 352 or through the bio-analysis module 350. Release of the controlled substance may involve controlling aspects of the mechanical structures described in U.S. patent application Ser. No. 13/934,845, which is incorporated herein by reference. For example, structures such as a regulator, securable opening, access mechanism, exit path, receiving portion, lockable opening, receiving path, dividing plate, a cover, lower dispensing portion, limiting/distributing device, various motors, gears and wheels, timers, electronic lock, secure lock, and other structures indicated in the application may be controlled in conjunction with biofeedback applications described herein. The software 346 may be stored in memory of a microcontroller that is housed within the secure dispensing device. Alternatively, or in addition, the software 346 may be stored in the remote server 330 and accessed over the network 328.

FIG. 6 depicts an embodiment of a method 466 of altering a dispensation parameter of a controlled substance from a secure dispensing device. In particular, FIG. 6 depicts an embodiment including varying the quantity of controlled substance dispensed, however, it should be understood that other dispensation parameters may be altered. The method 466 may include receiving prescription bioinformation 468. The received prescription bioinformation may be compared against stored prescriptions or other dispensation plans to determine if a dispensation parameter should be adjusted. A relative dispensation parameter may be calculated relative to an initial dispensation parameter. If the amount or other dispensation parameter is to be changed ("Yes" in decision block 470), then the changed amount is released 472 or the controlled substance is dispensed according to the adjusted dispensation parameter in lieu of the initial dispensation parameter. If the amount is not to be changed ("No" in decision block 470), then the original amount is released 474. Instead of releasing the same amount, no amount may be released. Dotted lines in FIG. 6 further indicate steps that may be added if authentication is required. Following a decision to change ("Yes" in decision block 470) the amount, authentication information is received 476. Authentication information may include, for example, a biometric identifier. If the authentication information is accepted ("Yes" in decision block 478), then the changed amount is released 472. If the authentication information is not accepted ("No" in decision block 478), then no amount is released 480. Alternatively, the original amount may still be released after an authentication failure.

Figure 7:
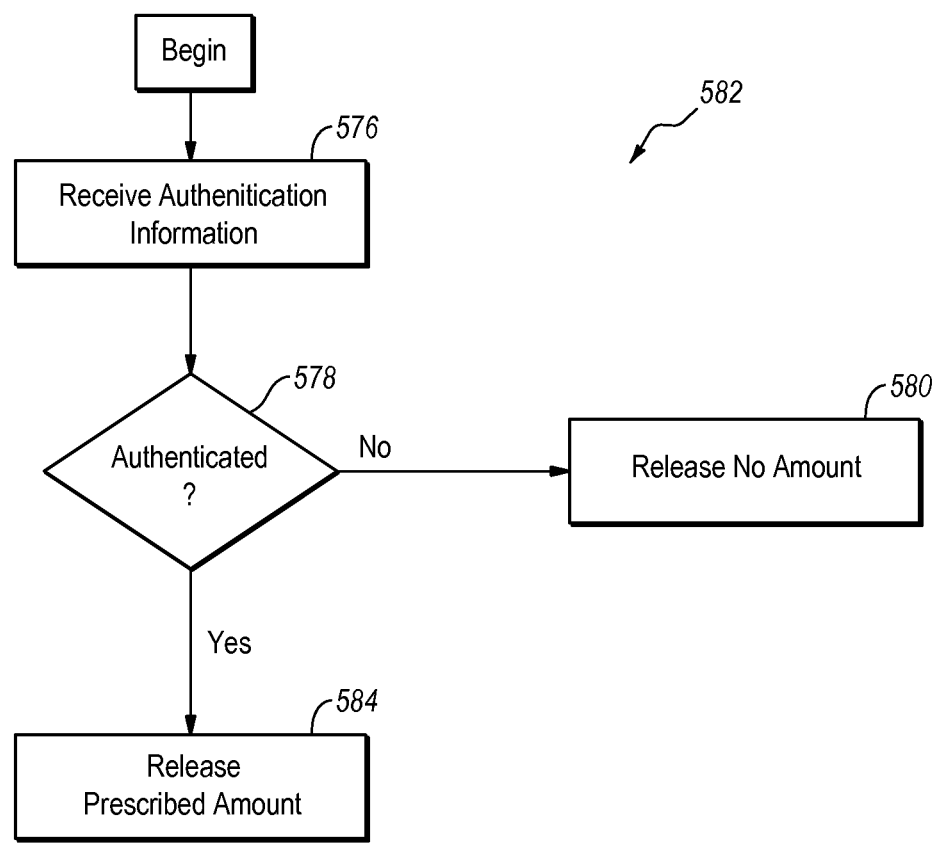
FIG. 7 is a flowchart illustrating a method for releasing a controlled substance based upon authentication.

FIG. 7 illustrates a flowchart for a method 582 of authenticating the user and releasing the prescribed amount. In FIG. 7, the method 582 may include receiving the biometric identifier 576. In FIG. 7, if the biometric identifier is authentic ("Yes" in decision block 578), then the prescribed amount is released 584. If the authentication information is not accepted ("No" in decision block 578), then no amount is released 580. Changing third party privileges may include one or more of the same rights provided to the doctor, different rights completely, or a mixture of both rights. The doctor may modify and eliminate the rights to third parties as desired. In an embodiment, a different entity from the doctor may grant, modify, and eliminate rights for the doctor and/or the third party care providers.

Examples of third party care providers who may be granted third party privileges to the dispensing device include a different doctor, a caregiver, friend, family member, therapist, health care worker, pharmacist, nurse, non-professional contact, parole officer, psychiatrist, physical therapist, dentist, veterinarian, medical professional, physician's assistant. In some embodiments, multiple parties may be granted third party privileges. Note that third party privileges may be valuable in overriding errors, for example, errors regarding changes made to the controlled substance by a doctor.

The secure dispensing device may include a one or more security features to limit and/or prevent the abuse or misuse of the controlled substance outside of the parameters of the prescription or other instructions for use. In some embodiments, the secure dispensing device may be locked or otherwise rendering inoperative upon the occurrence of a suspicious event. In other embodiments, the secure dispensing device may be connected to a network capable of providing notifications and/or updates to a user or a care provider upon the occurrence of a suspicious event. In yet other embodiments, the secure dispensing device may be locked or otherwise rendering inoperative and a notification and/or update may be provided to a user or a care provider.

Figure 8:
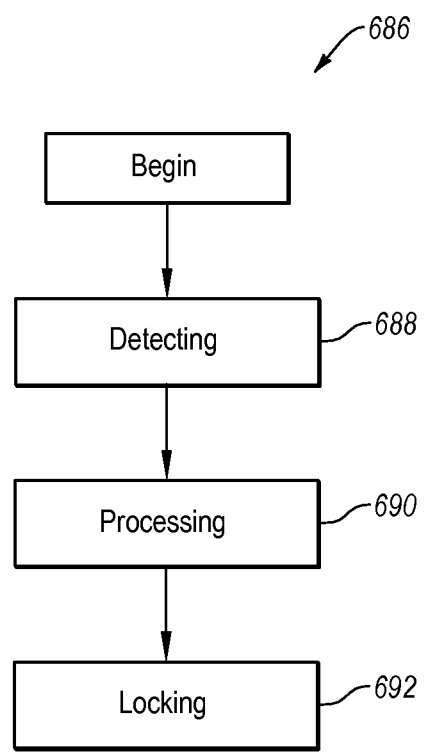
FIG. 8 is a flowchart illustrating a method of communication status information for evaluation and response.

For example, FIG. 8 depicts a flowchart of a method 686 for securing a secure dispensing device. The method 686 may include detecting 688 a change in one or more states of the secure dispensing device using a sensor to produce state information. In some embodiments, detecting 688 a change in one or more states of the secure dispensing device using a sensor may include detecting 688 a change in a location of the secure dispensing device such as via a global positioning system ("GPS") device in the secure dispensing device or a relative location of the secure dispensing device relative to a biometric sensor; detecting 688 a change in acceleration of the secure dispensing device such as via one or more accelerometers and/or gyroscopes in the secure dispensing device as described herein; detecting 688 a change in force applied to the secure dispensing device such as via a force sensor (e.g., piezoelectric, capacitive, displacement, or other type of force sensor) configured to measure force applied to the housing of the secure dispensing device; detecting 688 a change in a temperature of the secure dispensing device such as via a temperature sensor internal to secure dispensing device, external to secure dispensing device, or both; detecting 688 a change in an integrity of the housing, such as via a voltmeter measuring potential through a metal film distributed on the housing such that severing the metal film may result in a corresponding potential change, detecting 688 a change in usage frequency of the secure dispensing device may include monitoring the frequency with which information is input into a keypad or other input device of the secure dispensing device such as a quantity of failed access attempts within a predetermined period of time; or detecting 688 changes in other states of the secure dispensing device to produce state information.

The method 686 may include processing 690 the state information. Processing 690 the state information may include communicating the state information from the appropriate sensor to a microprocessor in the secure dispensing device or in a remote computing device such as a server or in a remote computer (such as server 224 or computing device 232 described in relation to FIG. 3). Processing 690 the state information may further include using the software 400 described in relation to FIG. 4. In some embodiments, the state information may be processed to compare the state information against a threshold value or range of values and determining whether the state information indicates that the state of the secure dispensing device is outside of acceptable parameters of use. The method 686 may include locking 692 the secure dispensing device upon the state information exceeding the threshold value or range of values, such as by sending a lock command from the microprocessor to actuate a locking motor in the secure dispensing device.

In some embodiments, the method 686 may create a geofence for use of the secure dispensing device, meaning if a location of the secure dispensing device is detected outside of a predetermined range of locations, the secure dispensing device may lock or be otherwise rendered inoperable. In the event the secure dispensing device is stolen or otherwise removed from the user or patient's home or care center, the secure dispensing device may automatically lock. In other embodiments, the method 686 may determine tampering with the secure dispensing device by comparing state information from an accelerometer to a threshold value to determine if an individual has attempted to break the secure dispensing device or otherwise impacted the secure dispensing device in an effort to access the controlled substance without authorization. For example, if the accelerometer reads an acceleration of greater than 10 times gravitational acceleration (10 gs) or other threshold value, the microprocessor processing the state information from the accelerometer may send a lock command to the secure dispensing device.

In yet other embodiments, the method 686 may lock the secure dispensing device when a force applied to the housing of the secure dispensing device exceeds a threshold value independent of acceleration of the secure dispensing device. For example, application of force to the housing by a vise may compress andor damage the housing without imparting significant acceleration to the secure dispensing device. The microprocessor may send a lock command to actuate a locking motor in the secure dispensing device upon receiving state information from a force meter indicating force applied in excess of, for example, 100 pounds (445 Newtons) or other threshold value. In yet further embodiments, the method 686 may lock the secure dispensing device when a temperature of the secure dispensing device andor housing exceeds a threshold value. For example, if a temperature sensor in the secure dispensing device detects temperatures in excess of 130° Fahrenheit (54° Celsius), the state information sent to the microprocessor may exceed the threshold value for temperature and the secure dispensing device may lock.

In yet other embodiments, the method 686 may lock the secure dispensing device when the housing is cut, pierced, or otherwise ruptured. For example, a volt meter may measure a potential across one or more conductive wires or a conductive foil located in or on the housing of the secure dispensing device and may detect a change in state when the one or more conductive wires or conductive foil is broken or interrupted, possibly due to an attempt to tamper with the secure dispensing device. State information may be sent to the microprocessor when a potential across the one or more conductive wires or conductive foil increases above a given threshold. In yet further embodiments, the method 686 may lock the secure dispensing device upon recognizing a change in the usage state of the secure dispensing device. For example, the secure dispensing device may log the number of access attempts via a keypad or other input device in a predetermined period of time. If the keypad or other input device receives more than 3, 5, 7, 10, or more access attempts within any of 10 seconds, 30 seconds, 1 minute, 3 minutes, 5 minutes, 10 minutes, or other duration of time, state information may be sent to the microprocessor indicating repeated access attempts and the microprocessor may send a lock command to actuate the locking motor in the secure dispensing device.

Locking 692 the secure dispensing device may include sending a lock command to actuate a locking motor to put the secure dispensing device in a locked state. The lock command may originate at the microprocessor, which may be local to the secure dispensing device or in a remote server or computing device, as described herein. Locking 692 the secure dispensing device may include allowing the secure dispensing device to remain in a locked state until an unlock command is provided by the microprocessor. In some embodiments, the microprocessor may provide the unlock command at a preset lock interval from the lock command being sent. The lock interval may be in a range having upper and lower values including any of 30 seconds, 1 minute, 5 minutes, 10 minutes, 30 minutes, 1 hour, 12 hours, or any value therebetween. For example, the lock interval may be in a range of 30 seconds to 12 hours. In another example, the lock interval may be in a range of 1 minute to 1 hour. In yet another example, the lock interval may be 10 minutes. In other examples, the lock interval may increase or otherwise vary depending on the number of lock commands previously sent by the microprocessor. For example, upon receiving a first state information exceeding a first threshold value, the microprocessor may send a first lock command with an associated first lock interval that is 1 minute. Upon receiving a second state information exceeding a second threshold value, the microprocessor may send a second lock command with an associated second lock interval that is 5 minutes.

In other embodiments, the microprocessor may provide the unlock command upon receiving a second state information below andor within the threshold value. For example, a lock command provided by the microprocessor after processing a first state information may put the secure dispensing device in a locked state, and the secure dispensing device may remain in the locked state until a second state information indicating a state of the secure dispensing device below andor within the threshold value. The microprocessor may process the second state information received from one or more sensors and provide the unlock command to a locking motor.

In yet other embodiments, the microprocessor may provide the unlock command to the locking motor upon receiving an unlock request from a remote server or computing device controlled by a care provider. For example, one or more sensors detecting 688 a state change in the secure dispensing device may provide state information to the microprocessor, and the microprocessor processing 690 the state information may result in locking 692 the secure dispensing device due to an individual attempting to access the controlled substance in the secure dispensing device outside of the parameters of a prescription. The secure dispensing device may remain in a locked state until a care provider is able to contact the patient and confirm the patient's condition andor possession of the secure dispensing device before the care provider decides to issue an unlock request to the secure dispensing device.

Figure 9:
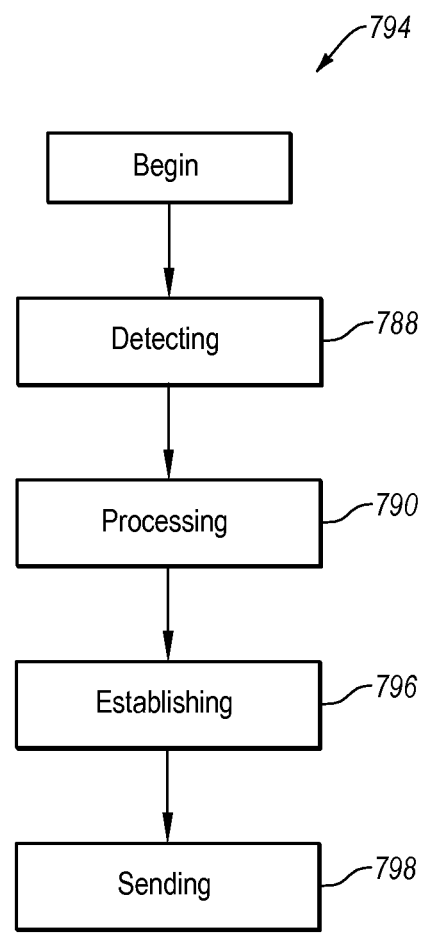
FIG. 9 is a flowchart illustrating a method of communicating alerts to one or more care providers.

FIG. 9 depicts a flowchart illustrating a method 794 of communication alerts to one or more care providers. The method 794 may include detecting 788 a change in state of the secure dispensing device and processing 790 the associated state information in a microprocessor, in a manner similarly to or the same as described in relation to FIG. 8. The method 794 further includes establishing 796 communication with a care provider's device, such as a computing device andor server connected to a data network as described in relation to FIGS. 2 and 3, a cellular phone capable of receiving SMS text messages, another telephone capable of receiving a recorded message, other communication device in the possession or control of a care provider and then sending 798 an alert communication to the care provider. As used herein an "alert communication" may be any communication that may provide a care provider with a unique identification of the secure dispensing device originating the state information and, optionally, information related to the detected state change.

In some embodiments, the method 794 may detect a quantity of access attempts exceeding a defined threshold value and send an alert communication to a care provider informing them that the patient has exceeded the access attempt threshold. In other embodiments, the method 794 may detect a particular acceleration of the secure dispensing device exceeding a threshold value and send an alert communication to a care provider informing them that the secure dispensing device has experienced an acceleration of the particular detected value. In yet other embodiments, the method 794 may detect a rupture in the integrity of the housing of the secure dispensing device and send an alert communication to a care provider informing them that the housing has been opened. In yet further embodiments, the method 794 may detect a failure to access the secure dispensing device and send an alert communication to a care provider informing them that the controlled substance has not be administered according to the intended parameters.

Figure 10:
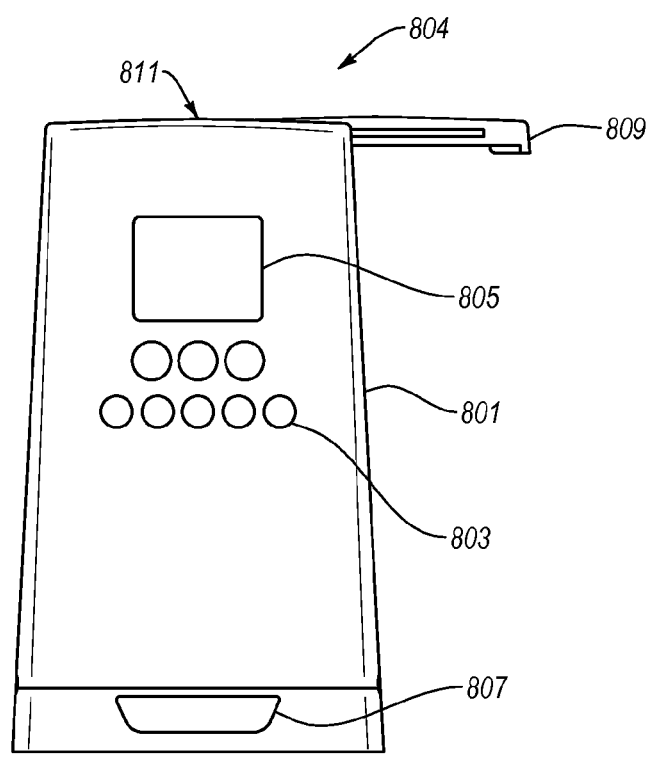
FIG. 10 is a front view of an embodiment of a secure dispensing device.
Figure 11:
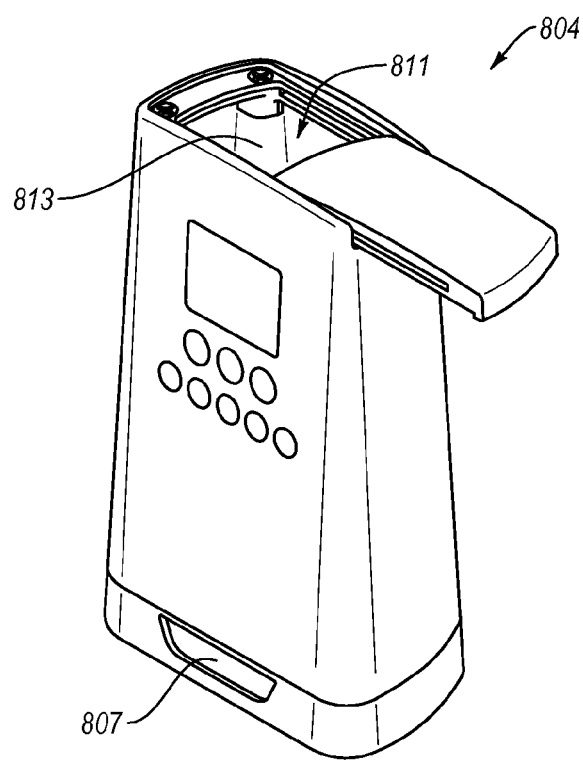
FIG. 11 is a perspective view of the embodiment of a secure dispensing device of FIG. 10.

FIGS. 10 and 11 illustrate an embodiment of a secure dispensing device 804 having a substantially flat face and back. The housing 801 of the secure dispensing device 804 may be substantially break resistant. As used herein, "break resistant" should be understood to encompass housings that may withstand at least 40,000 pounds (178 Kilonewtons) across the median of the apparatus. The housing 801 may include a plurality of components, or may be substantially monolithic. The housing 801 may be made of or include plastics, resins, nylon, metals, rubbers, polymers, polyresins, alloys, carbon fiber, acrylic, polycarbonate, polyester, PET, PETG, KEVLAR, LEXAN, carbon fiber composites, NALGENE, ACRYLITE, DURAPLEX, HYGARD, MAKROLON, MICARTA, NYLATRON, other materials, or combinations thereof. The secure dispensing device 804 may include one or more input devices 803, such as a keypad or other input devices described herein. The input devices 803 may allow a user to input or otherwise communication information to the secure dispensing device 804 for access, operation, status, authentication, other purposes, or combinations thereof. A display 805 on the secure dispensing device 804 may allow the secure dispensing device 804 to communicate information such as for access, operation, status, authentication, other purposes, or combinations thereof to a user. The display 805 may be a visual display, as shown in FIG. 10, but is not limited to a visual display and may be or include a tactile display andor auditory display. The housing 801 may have an opening 807 in communication with an exit path as described herein. The opening 807 may be sized to allow the controlled substance contained within the secure dispensing device 804 to be delivered to a user or patient. The housing 801 of the secure dispensing device 804 may also include a lockable cover 809 that is lockable relative to the housing 801. When unlocked and moved to an open state, the lockable cover 809 may reveal an access opening 811. In some embodiments, the access opening 811 may be substantially the area of a top of the secure dispensing device 804. In other embodiments, the access opening 811 may be sized to limit a user's ability to access the contents of the secure dispensing device 804.

As shown in FIG. 11, the access opening 811 may provide communication with an access compartment 813. The access compartment 813 may be configured to hold the controlled substance in storage until dispensation. In some embodiments, the access compartment 813 may be configured to hold a month's supply of the controlled substance. For example, the access compartment 813 may be configured to hold 180 hydrocodone tablets. In some embodiments, the access compartment 813 may be configured to be opened only by the pharmacist, preventing a user or other individual from accessing the controlled substance therein outside of the parameters of the prescription or other dispensation plan.

Embodiments described herein may comprise or utilize a special purpose or general-purpose computer including computer hardware, such as, for example, one or more processors and system memory. Embodiments described herein also include physical and other computer-readable media for carrying or storing computer-executable instructions andor data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: computer storage media and transmission media.

Computer storage media includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems andor modules andor other electronic devices. When information is transferred or provided over a network or another communications connection (either hardwired, wireless, or a combination of hardwired or wireless) to a computer, the computer properly views the connection as a transmission medium. Transmissions media can include a network andor data links which can be used to carry or desired program code means in the form of computer-executable instructions or data structures and which can be accessed by a general purpose or special purpose computer. Combinations of the above should also be included within the scope of computer-readable Emedia.

Further, upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM andor to less volatile computer storage media at a computer system. Thus, it should be understood that computer storage media can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features andor methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A secure dispensing device with biofeedback, the secure dispensing device comprising:
 a housing that includes an access compartment with a controlled substance, the controlled substance including a first amount of the controlled substance to be dispensed;
 an exit path that includes an opening that is sized for the controlled substance to be released outside of the access compartment;
 a regulator that releases the controlled substance from within the housing;
 an authentication receiver configured to determine if a biometric identifier is associated with the secure dispensing device, the authentication receiver configured to authenticate a user with a plurality of authentication inputs, at least one authentication input of the plurality of authentication inputs being the biometric identifier; and
 a controller configured to receive prescription bioinformation about the user from an external source and process the prescription bioinformation to determine a second amount of the controlled substance to be dispensed, the first amount and the second amount of the controlled substance to be dispensed being different, and the controller configured to change access rights of one or more users based at least in part on the prescription bioinformation.

2. The secure dispensing device of claim 1, wherein the controller receives the prescription bioinformation in a real-time manner.

3. The secure dispensing device of claim 1, wherein the biometric identifier is a passive biometric identifier.

4. The secure dispensing device of claim 3, wherein the passive biometric identifier is obtained with no interaction by the user.

5. The secure dispensing device in claim 1, wherein the prescription bioinformation is obtained using at least one of a graphene-based sensor, pulse oximetry, a contact microphone, blood-based microliter lab, facial recognition technology, unique heart wave, bodily gestures, cholesterol levels, ph levels, bodily movement, sweat, muscle activity, breathing rate, skin temperature, posture, electrical changes in skin, facial expression, hydration level, and a urine sample.

6. The secure dispensing device in claim 1, wherein the prescription bioinformation is obtained by using at least one of an adhesive bandage, sensor that snaps to clothing, custom clothing, thermal underwear, underclothing, fabric sensor in a strap or clothing form, belt, waist band, chest band, wrist band, watch, camera on a watch, headset, sensor attached to asthma inhaler, ingestible sensor, non-invasive skin permeable sensor, gel insole, and earbuds.

7. The secure dispensing device of claim 1, wherein the controller is configured to be in data communication with a computer network wherein the prescription bioinformation may be stored and transmitted by the controller.

8. The secure dispensing device of claim 1, wherein the access rights include access rights to one or more of an amount of the controlled substance, a period of time between accessing the controlled substance, and a time of day for accessing the controlled substance.

9. A method of dispensing one or more controlled substances housed within a secure dispensing device, the method comprising:
  receiving prescription bioinformation about a user from an I/O module;
  comparing the received prescription bioinformation with stored prescription information regarding the one or more controlled substances to produce a relative dispensation parameter;
  changing an initial dispensation parameter of the one or more controlled substances to an adjusted dispensation parameter of the one or more controlled substances based on the relative dispensation parameter, the initial dispensation parameter and adjusted dispensation parameter being different;
  changing access rights to the one or more controlled substances for one or more users based at least in part on the relative dispensation parameter; and
  releasing a prescription of the one or more controlled substances according to the adjusted dispensation parameter.

10. The method of claim 9, wherein changing the initial dispensation parameter includes one or more of changing a dispensation quantity, changing a dispensation time, and changing the one or more controlled substances to be dispensed.

11. The method of claim 9, further comprising authenticating the user using a biometric identifier.

12. The method of claim 9, further comprising removing access rights from the user and granting access rights to a third party.

13. The method of claim 9, further comprising overriding the adjusted dispensation parameter, overriding being performed by the user or a third party based on access rights granted.

14. The method of claim 9, further comprising transmitting the received prescription bioinformation from the secure dispensing device via a network to a remote microprocessor in a remote computing device or server, wherein the remote microprocessor transmits the adjusted dispensation parameter via the network to the secure dispensing device.

15. A secure dispensing device with biofeedback, the secure dispensing device comprising:
  a housing that includes an access compartment configured to hold one or more controlled substances;
  an exit path that includes an opening that is sized for the one or more controlled substances to be released outside of the access compartment;
  a regulator configured to release the one or more controlled substances from within the housing; and
  a controller configured to receive prescription bioinformation about a user from an external source and process the prescription bioinformation to determine a prescription to release, wherein if the secure dispensing device does not contain a controlled substance from the prescription, the secure dispensing device notifies the user, wherein the controller is configured to change access rights of one or more users based at least in part on the prescription bioinformation.

16. The secure dispensing device of claim 15, wherein the controller is configured to authenticate the user using bioinformation and at least one other identifier.

17. The secure dispensing device of claim 16, wherein the at least one other identifier is a biometric identifier.

18. The secure dispensing device of claim 15, wherein the one or more users includes a third party that is a health care provider, and wherein the health care provider can override the controller.

19. The secure dispensing device of claim 15, wherein the access rights include access to two or more controlled substances.

20. The secure dispensing device of claim 15, wherein the access rights include access rights to one or more of an amount of the controlled substance, a period of time between accessing the controlled substance, and a time of day for accessing the controlled substance.

* * * * *